United States Patent [19]
Hellon

[11] Patent Number: 4,623,308
[45] Date of Patent: Nov. 18, 1986

[54] FREE STANDING BASE MOLD
[75] Inventor: Keith Hellon, Libertyville, Ill.
[73] Assignee: MacLean-Fogg Company, Mundelein, Ill.
[21] Appl. No.: 801,563
[22] Filed: Nov. 25, 1985

Related U.S. Application Data

[63] Continuation-in-part of Ser. No. 600,775, Apr. 16, 1984, abandoned.

[51] Int. Cl.⁴ .......................... B29C 1/00; B29C 1/14
[52] U.S. Cl. ....................................... 425/117; 249/83; 249/160
[58] Field of Search ................. 249/83, 117, 160, 127; 425/117, 173

[56] References Cited
U.S. PATENT DOCUMENTS

| Re. 28,165 | 9/1974 | McCormick | 425/117 |
| 2,718,126 | 9/1955 | Ball | 249/127 X |
| 2,996,762 | 8/1961 | McCormick | 425/117 X |
| 3,014,614 | 12/1961 | Carroll et al. | 249/160 X |
| 3,483,904 | 12/1969 | Donovan | 249/127 X |
| 3,940,219 | 2/1976 | Pickett et al. | 425/117 |
| 3,982,862 | 9/1976 | Pickett et al. | 425/117 |
| 4,272,049 | 6/1981 | Kindel | 425/173 X |

*Primary Examiner*—J. Howard Flint, Jr.
*Attorney, Agent, or Firm*—Mason, Kolehmainen, Rathburn & Wyss

[57] ABSTRACT

The base mold is made from a single sheet of plastic material and is adapted to receive a specimen and either (1) a tissue processing cassette, or (2) an embedding ring. A fluid/solid fixation material is poured into the base mold and allowed to solidify in order to fix the specimen to and adjacent an outer bottom surface of the cassette or the embedding ring while the cassette or embedding ring is being supported by the base mold. The base mold includes a cassette/embedding ring supporting panel and a tissue receiving receptacle integral with and depending from the supporting panel. The base mold further includes a support formation integral with and depending from the cassette supporting panel. The support formation extends at least part way around the receptacle and includes a lower edge disposed in one plane to provide a sturdy supporting edge for supporting the base mold on a planar surface. In one embodiment, for use with an embedding ring having a relatively small tissue-receiving receptacle, the supporting panel includes a continuous slot or recess completely surrounding the receptacle to prevent overflow of the fixation material past a continuous flange extending downwardly from an embedding ring and received within the continuous slot.

16 Claims, 10 Drawing Figures

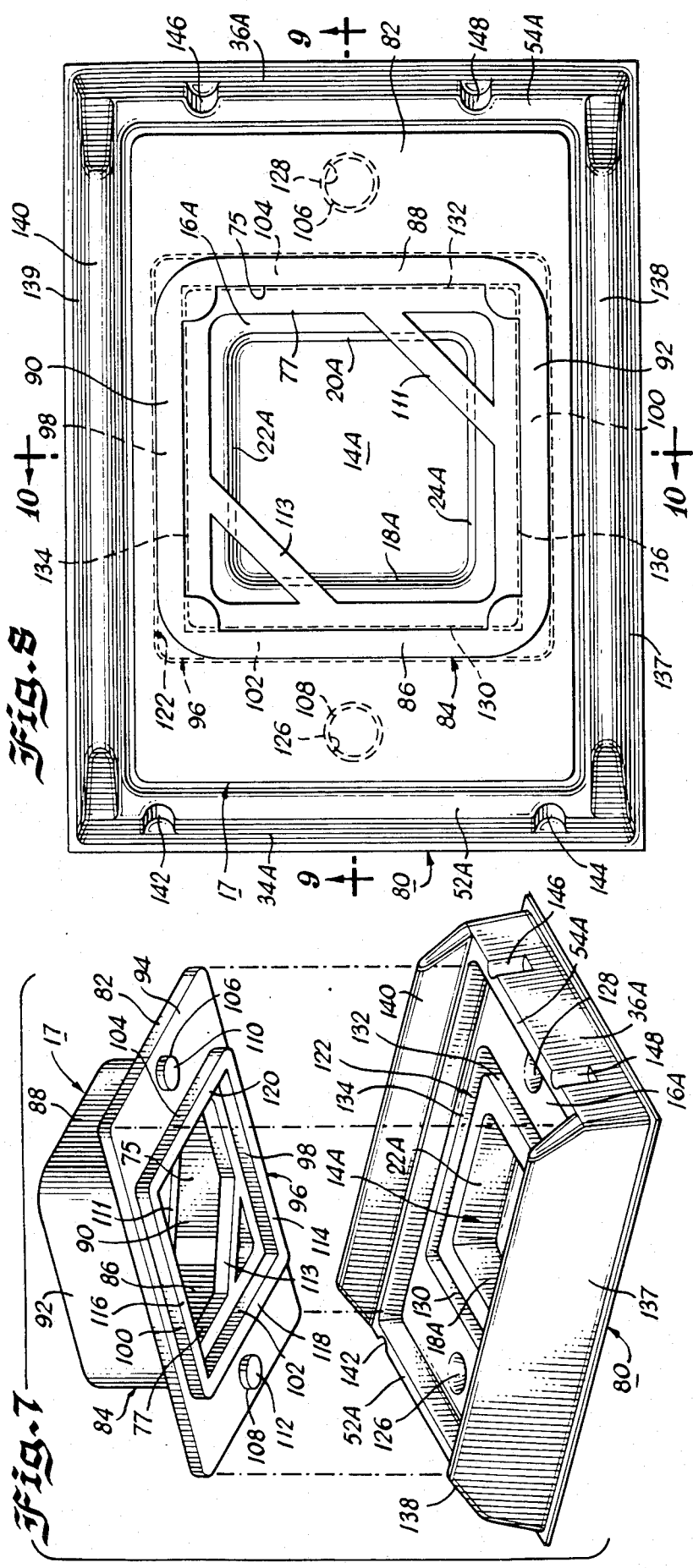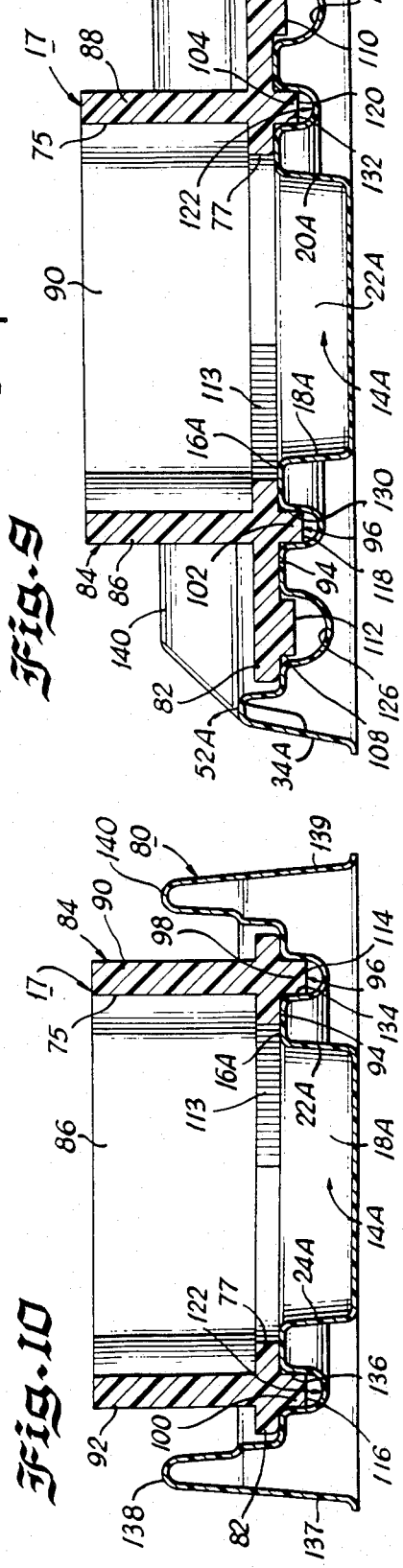

FREE STANDING BASE MOLD

RELATED APPLICATION

This application is a continuation-in-part of copending U.S. patent application Ser. No. 600,775, filed Apr. 16, 1984, for FREE STANDING BASE MOLD by the applicant herein and now abandoned.

BACKGROUND OF THE INVENTION

A. Field of the Invention

The present invention relates to a disposable unitary plastic base mold made from a sheet of plastic material and adapted to receive a biological tissue specimen and to support a tissue processing cassette or a tissue processing embedding ring. A solidifiable fluid embedding material, such as paraffin, is poured into the mold through the cassette or through the embedding ring and the embedding material is allowed to solidify in order to encapsulate the specimen and fix the tissue specimen to and adjacent an outer bottom surface of the cassette or embedding ring.

B. Description of the Prior Art

Heretofore, various molds for embedding tissue specimens therein have been proposed. Examples of such previously proposed molds are disclosed in the following U.S. Pat. Nos.:

| | |
| --- | --- |
| Re. 28,165 | McCormick |
| 2,718,126 | Ball |
| 3,014,614 | Carroll, et al |
| 3,483,908 | Donovan |
| 4,272,049 | Kindel |

The McCormick U.S. Reissue Pat. No. Re. 28,165 discloses a biological specimen processing and embedding apparatus comprising a combination capsule and base mold apparatus for treatment of a biological specimen. The base mold is formed from metal and has a generally open-top box-like rectangular shape into which a multi-purpose capsule and open mold member is received. The base mold includes a flat bottom wall, two transverse side walls, two longitudinal side walls, and an open top, the upper portion of the side walls being offset outwardly to form an angular horizontal surface or ledge with the open top.

The Ball U.S. Pat. No. 2,718,126 discloses an ice mold for dental use made of plastic or rubber for the formation of ice cubes of a configuration substantially similar to that of the prescribed areas of the mouth in order that it may be inserted into the patient's mouth. More particularly, the mold is formed with a recessed portion or cavity having a configuration of the arc of a circle, a recessed portion having a configuration of greater curvature substantially approaching a semi-circular shape, and a third cavity having a substantially rectangular shape, all having a substantially rounded or concaved bottom adapted to be filled with water and placed in a freezing compartment.

The Carroll, et al U.S. Pat. No. 3,014,614 discloses a disposable plastic mold adapted for embedding samples of tissue in paraffin wherein the molded material can be easily and quickly removed. The disposable mold comprises a plurality of rectangular mold containers, or cups, each having an open upper surface and are joined in clusters of twelve containers by joining straps which connect each of the containers to each adjacent container. If the material is to be formed while the containers are resting upon their bottom surfaces, protrusions are formed on the lower walls of each of the containers in order to facilitate resting of the containers on a planar surface.

The Donovan U.S. Pat. No. 3,483,908 discloses a flexible container including a side wall provided with a series of substantially parallel ribs which provide increased resistance to deformation in the lateral direction. A bottom wall is also provided having a spiral groove spiralling outwardly from the center of the bottom wall to provide a discharge means in combination with the ribbed wall for removing a substantially solid substance, such as a cupcake, from the container by pressing the bottom wall of the container upwardly.

The Kindel U.S. Pat. No. 4,272,049 discloses a mold for molding specimen blocks to be cut in a microtome or an ultramicrotome. The mold comprises a plate which is made from a heat resistant plastic and which has a number of cavities open at their ends. The cavity has a general cylindrical shape. A transparent bottom wall is provided for examination of the tissue specimen therein and which is thin enough so that it can be deformed easily to remove a molded block therefrom when subjected to finger pressure.

In addition to the molds described above, other disposable specimen molds have been proposed which are formed from a single sheet of plastic material. Such a mold includes a planar sheet of plastic of a generally square or rectangular shape and having a centrally located recess or receptacle pressed from or formed in the sheet. The receptacle comprises four side walls and a bottom wall wherein the sole means of support for the mold is the bottom wall of the receptacle.

As will be described in greater detail hereinafter, the free standing base mold of the present invention differs from the various mold containers previously proposed by providing a base mold which includes means for sturdily supporting the base mold upon a planar surface, as well as means for receiving a biological tissue specimen and for supporting a tissue processing cassette or an embedding ring while a solidifiable fluid embedding material is poured into the mold and allowed to solidify in order to fix the tissue specimen to and adjacent an outer bottom surface of the cassette or the embedding ring.

SUMMARY OF THE INVENTION

According to the present invention there is provided a disposable unitary plastic base mold made from a sheet of transparent plastic material and adapted to receive a specimen and either (1) a cassette or (2) an embedding ring for supporting same while a fluid/solid fixation material is poured into the mold and allowed to solidify to fix the specimen to and adjacent an outer bottom surface of the cassette or embedding ring. The mold is a free standing, disposable, unitary base mold formed entirely of press molded, thin, transparent plastic sheet material and has a generally rectangular shaped outer peripheral support wall structure formed with a continuous, supporting lower edge adapted to rest upon a planar surface for supporting the base mold thereon during use. To achieve the full advantage of the present invention, the plastic material forming the base molds are transparent for initial proper orientation of the tissue specimen within a specimen receiving cavity. Proper initial orientation of the specimen is needed so that the specimen is aligned properly for exact right angle cuts and so that the specimen can be sliced in a plane of maximum surface area. The base mold includes a first recess forming a lower mold receptacle having a generally rectangular peripheral outline for containing a tissue specimen to be embedded in a tissue embedding material flowed into the lower mold receptacle from above while in a fluid condition and solidifying around the specimen to secure the specimen in a fixed position within the lower mold receptacle. The lower mold receptacle includes a planar bottom wall having an underside in coplanar relation with the lower edge of the support wall structure to also rest on the planar surface. The bottom wall has a continuous, outer peripheral edge spaced apart inwardly from the lower edge of the support wall structure and integrally joining an upstanding peripheral side wall. The base mold further includes a second recess forming an upper mold receptacle for receiving a tissue cassette or an embedding ring placed therein after placement of the tissue specimen in the lower mold receptacle. The tissue cassette or embedding ring being of a type having an embedding material-containing support structure having at least one aperture therein for communication between the upper and lower mold receptacles for permitting at least some of the fluid embedding material poured into the upper mold receptacle to flow through the aperture into the lower mold receptacle to embed the tissue specimen in the material and fix the material to the cassette or embedding ring.

The upper mold receptacle includes a lower support panel for supporting the cassette or embedding ring. The support panel is spaced parallel and above the bottom wall for integrally joining an upper peripheral edge of the upstanding peripheral side wall of the lower mold receptacle and extending outwardly thereof toward the support wall structure. The lower panel of the upper mold receptacle integrally joins an upstanding peripheral side wall forming the upper mold receptacle and the upstanding peripheral side wall of the upper mold receptacle is integrally joined to an upper peripheral rim of the support wall structure spaced outwardly around the upper mold receptacle. The peripheral rim of the upper mold receptacle integrally joins a downwardly and outwardly sloping, continuous peripheral skirt wall having the supporting lower edge of the base mold formed along the lower edge adapted to rest on the planar surface.

BRIEF DESCRIPTION OF THE DRAWINGS

FIG. 7 is an exploded perspective view of another embodiment of the free standing base mold and a typical embedding ring;

FIG. 8 is an elevated top view showing an embedding ring received within the base mold of FIG. 7;

FIG. 9 is a cross-sectional view taken along line 9—9 of FIG. 8; and

FIG. 10 is a cross-sectonal view taken along line 10—10 of FIG. 8.

DESCRIPTION OF THE PREFERRED EMBODIMENTS

Figure 1:
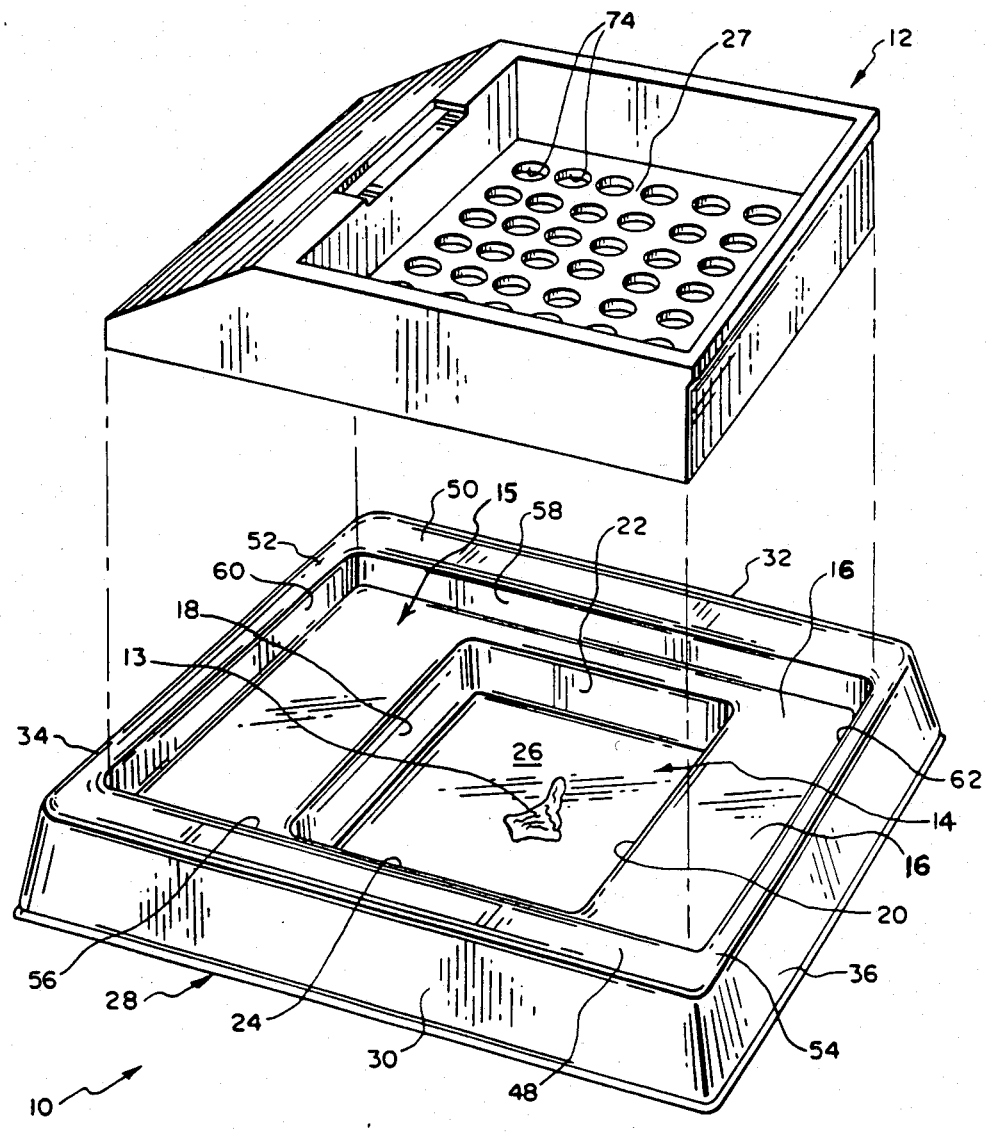
FIG. 1 is an exploded perspective view of the free standing base mold and a tissue specimen processing cassette with its cover removed.

Referring now to FIG. 1, there is illustrated therein a free-standing base mold 10 constructed according to the teachings of one embodiment of the present invention and a conventional tissue specimen processing cassette 12 (with its cover removed) adapted to be used with the base mold 10 in order to process and embed biological tissue specimens in an embedding material for subsequent preparation of thin section slices by cutting the specimens into thin sections on a microtome or an ultramicrotome for microscopic analysis.

In order to prepare a specimen 13 so that it can be cut into thin sections, the specimen 13 must first be processed in a fluid-permeable container in order to dehydrate the tissue, such as in the tissue specimen processing cassette 12 shown in FIG. 1. Then the specimen 13 is fixed to the cassette 12 by placing the specimen 13 in a lower mold receptacle, generally designated 16, of the base mold 10, placing the cassette in an upper mold receptacle, generally designated 15, over the specimen 13 in the lower mold receptacle 16, as shown in FIGS. 1 and 2, and pouring embedding material, such as paraffin wax, through the cassette 12 so that the wax hardens over the specimen 13 and onto the cassette 12.

Figure 3:
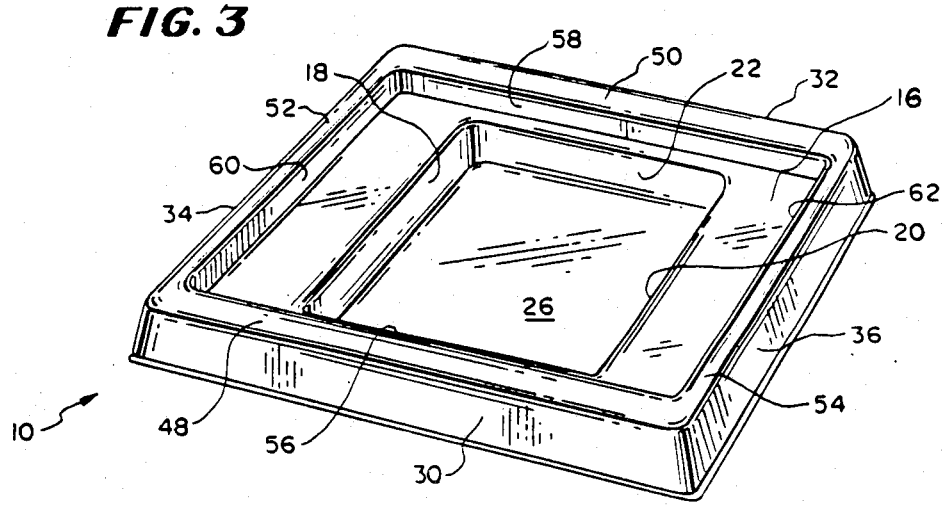
FIG. 3 is a perspective view of the free standing base mold shown in FIG. 1.
Figure 4:
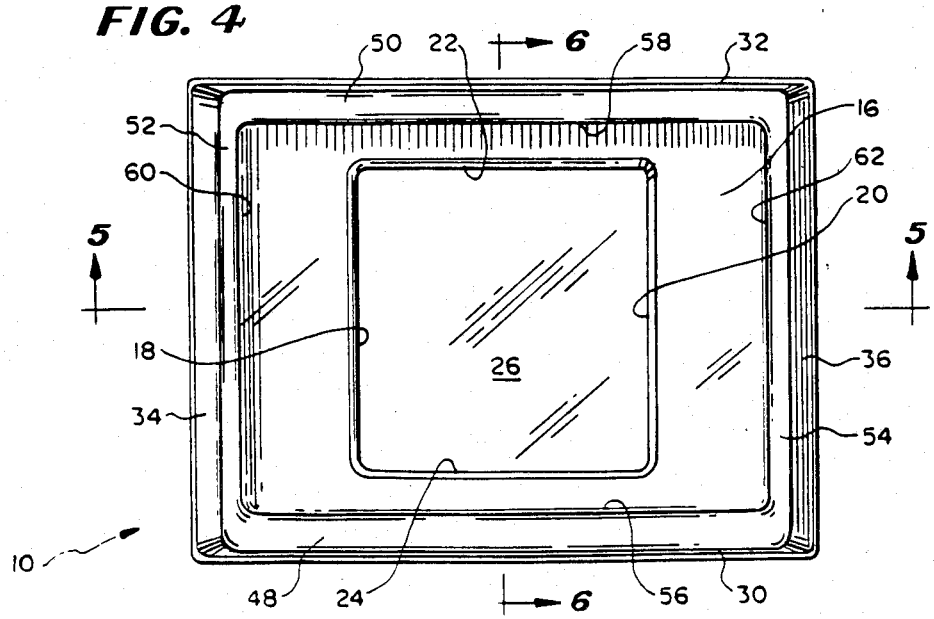
FIG. 4 is a top view of the base mold shown in FIG. 1.

Turning now to FIGS. 3 and 4, the free standing base mold 10 of the present invention is formed or press molded from a single sheet of plastic material, such as a polyvinyl, e.g. polyethylene or polypropylene, or any other suitable material which is stable at both high and low temperatures to which the base mold 10 may be subjected during the embedding process.

Figure 2:
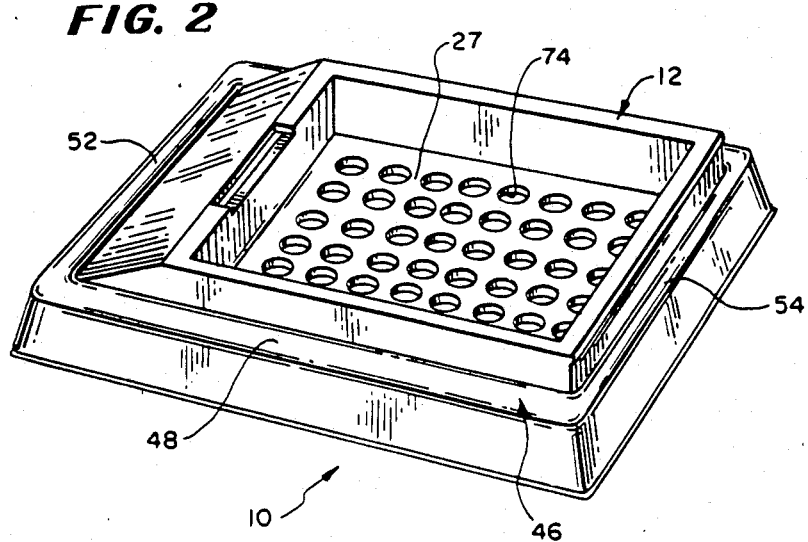
FIG. 2 is a perspective view of the free standing base mold having the tissue specimen processing cassette received thereon.

The base mold 10 includes a cassette or embedding ring supporting panel 14 onto which a cassette or embedding ring can rest, such as the tissue specimen processing cassette 12 shown in FIGS. 1 and 2 or the embedding ring 17 shown in FIGS. 7-10. The supporting panel 14 has depending therefrom and integral therewith the specimen and wax receiving lower mold receptacle 16. The lower mold receptacle 16 is defined between four side walls 18, 20, 22 and 24 and a planar bottom wall 26. A processed tissue specimen 13 is placed into the lower mold receptacle 16 and a cassette 12 or embedding ring 17 is disposed in the upper mold receptacle 15 over the specimen 13 supported on supporting panel 14 of the base mold 10, as shown in FIGS. 1 and 2. Paraffin wax or other similar solidifiable embedding material then is poured through the cassette 12 and over the specimen 13 in an amount sufficient to fix an outer surface of a bottom wall 27 of the cassette 12 to the solidifiable material or to fill a substantial interior portion of the embedding ring 17. The specimen 13, embedded in the solidifiable material, then is fixed to the outer surface of cassette bottom wall 27, or to the embedding ring 17 as will be described in more detail with reference to FIGS. 7-10.

Figure 5:
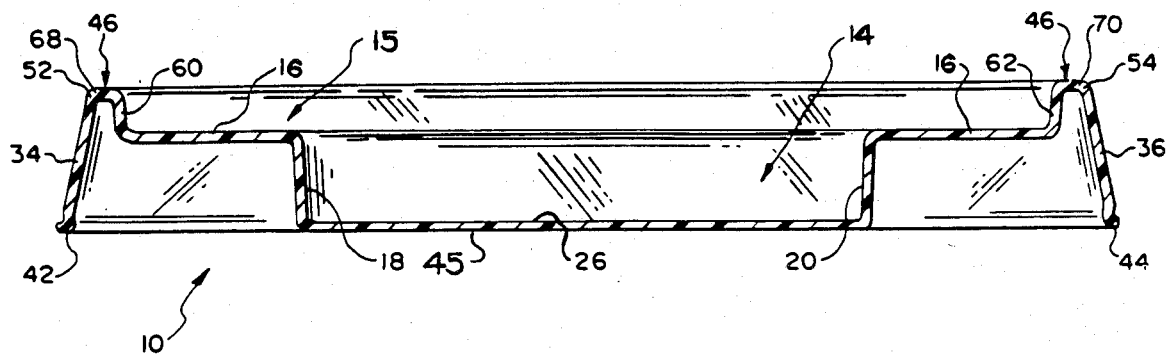
FIG. 5 is a vertical sectional view of the free standing base mold and is taken along line 5—5 of FIG. 4.
Figure 6:
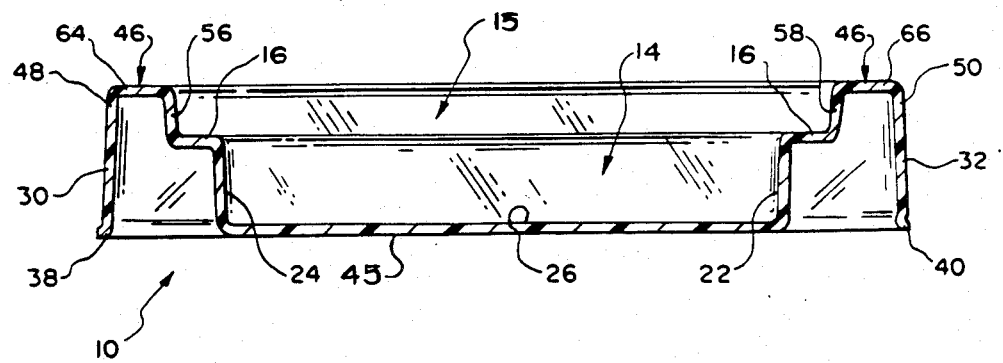
FIG. 6 is a vertical sectional view of the free standing base mold and is taken along line 6—6 of FIG. 4.

In accordance with an important feature of the present invention, the supporting panel 14 defining a lower surface of the upper mold receptacle 15, and the lower wall receptacle 16 are supported by a support formation 28 extending completely around the supporting panel 14 to define a lowermost planar edge. The support formation 28 is defined by a downwardly and outwardly sloping, continuous peripheral skirt wall, defined by four side walls, 30, 32, 34 and 36 each having a lower edge 38, 40, 42 and 44 respectively (FIGS. 5 and 6) which lie in the same plane to support and stabilize the base mold 10 on a planar working surface. It is to be understood that in accordance with an important feature of the present invention, the support formation 28 provides a sturdy support for the base mold 10.

To achieve the full advantage of the present invention, an outer surface 45 of the bottom wall 26 of the lower mold receptacle 16 is coplanar with the plane of the lower edges 38, 40, 42 and 44 of the side walls 30, 32, 34 and 36, respectively, to further support the base mold 10.

To enhance the support function, and to achieve the full advantage of the present invention, the four side walls 30, 32, 34 and 36 of the support formation 28 incline outwardly toward the lower edges 38, 40, 42 and 44 for supporting the base mold 10 on a planar working surface and to prevent the base mold 10 from tipping in the event it is abruptly disturbed during the embedding process.

The cassette supporting panel 14 is connected to the four side walls 30, 32, 34, 36 by a peripheral rim 46 which extends around the supporting panel 14. The rim 46 is defined by four wall portions 48, 50, 52 and 54 each having an inverted U-shaped cross-section. The wall portions 48, 50, 52 and 54 include an inner leg or upstanding peripheral side wall portion 56, 58, 60 or 62 formed integrally with and extending upwardly from the supporting panel 16, a curved bight portion 64, 66, 68 or 70 defining a base of the inverted U-shaped cross-section, joining the inner leg portions 56, 58, 60 and 62 to each of the side walls 30, 32, 34 and 36. An upper portion of the side walls 30, 32, 34 and 36 define outer leg portions of the inverted U-shaped wall portions 48, 50, 52 and 54.

The cassette supporting panel 14 and the upstanding peripheral side wall portions 56, 58, 60 and 62 define the cassette receiving upper mold receptacle 15. After the specimen 13 is placed in the lower mold specimen receiving receptacle 16, the tissue specimen processing cassette 12 (FIG. 2) or embedding ring 17 (FIGS. 9 and 10) is placed onto the support panel 14, to retain the cassette 12 or embedding ring 17 in place. The upstanding peripheral side wall portions 56, 58, 60 and 62 of the upper mold receptacle 15 define means for retaining the cassette 12 or embedding ring 17 in place and for retaining paraffin wax, or other embedding material, within the cassette/embedding ring receiving upper mold receptacle 15. The embedding material is poured through the cassette 12 or into the embedding ring 17 in an amount sufficient to substantially fill the specimen receiving lower mold receptacle 16 and enter the upper mold receptacle 15 so that the embedding material is adhered to at least an outer surface of the bottom wall 27 of the cassette 12, or to the embedding ring 17, upon solidification.

According to the teachings of the present invention, once a tissue specimen 13 has been properly dehydrated in a tissue specimen processing cassette 12 and is ready to be embedded in paraffin wax or other solidifiable embedding material, the specimen is removed from the cassette 12 and placed into the tissue receiving lower mold receptacle 16. The cassette 12 (FIG. 2) or embedding ring 17 (FIGS. 9 and 10) then is placed into the cassette receiving upper mold receptacle 15 and the paraffin wax is poured through openings 74 in the bottom wall 27 of the cassette 12 or through an upper skirt opening 75 in the embedding ring and flows into the tissue receiving lower mold receptacle 16 until the wax fills the tissue receiving lower mold receptacle 16 and flows into the upper mold receptacle 15 above the bottom wall 27 of the cassette 12 or in contact with and over an inwardly extending peripheral flange 77 of the embedding ring 17. When the wax solidifies, the cassette 12 or embedding ring 17 is separated from the base mold 10. The hardened wax and wax-embedded specimen 13 are firmly attached to the bottom wall 27 of the cassette 12 or to the embedding ring 17 and flange 77 thereof when the base mold is separated since the embedding material is solidified above and below the bottom wall 27 of the cassette 12 and within the openings 74.

Accordingly, the cassette 12 and the wax mold containing the fixed tissue specimen then can be placed into a chuck or other specimen holding mechanism of a conventional microtome of ultramicrotome for the cutting of thin sections of the tissue specimen.

It is apparent that one of the advantages of the free standing base molds 10 and 80 of the present invention, is that the base molds 10 and 80 can be sturdily supported on a planar surface by the lower edges 38, 40, 42 and 44 of the support formation 28 while a tissue specimen 13 is placed and orientated in the tissue receiving receptacle 16. Furthermore, once the cassette 12 is placed into the cassette receiving receptacle 72, the support formation 28 readily supports the base mold 10 while the base mold 10 rests on a conventional hot block during the pouring process of the paraffin wax embedding material, as well as during the cooling process of the embedding material while the base mold 10 rests on a conventional cold block.

Turning now to FIGS. 7-10, there is shown another embodiment of the base mold, generally designated 80, particularly adapted for receiving a commercially available embedding ring, generally designated 17. The commercially available embedding ring 17 generally includes a planar outwardly extending flange 82 and a generally rectangular skirt 84 extending upwardly from the flange 82 for receiving a fluid embedding material, such as paraffin wax. The skirt, generally designated 84, is defined by four integral upstanding wall portions 86, 88, 90 and 92. An undersurface 94 of the flange 82 includes a continuous downwardly extending wall structure 96 extending perpendicularly downwardly from the undersurface 94 of the flange 82 and is defined by four integral continuous wall portions 98, 100, 102 and 104. In addition, the embedding ring 17 includes a pair of spaced, downwardly extending round protrusions 106 and 108 extending downwardly from the undersurface 94 of the flange 82 having lowermost edges 110 and 112. The flange 82 also includes a pair of embedding material holding ribs 111 and 113 for the embedding material to solidify around for sturdy attachment of the embedding material to the embedding ring 17.

The operation of this commercially available embedding ring 17 with a commercially available base mold, is such that lower planar surfaces 114, 116, 118 and 122 of the downwardly extending flange wall portions 98, 100, 102 and 104, respectively, either rest upon a planar panel surrounding the tissue receiving lower mold receptacle (similar to lower mold receptacle 16 described with reference to FIGS. 1-6) or, if the tissue receiving receptacle is large enough, the downwardly extending walls 98, 100, 102 and 104 will be partially received within the tissue receiving lower receptacle with the lower planar surfaces 110 and 112 of the downwardly extending protrusions 106 and 108 resting upon the planar panel. The walls 98, 100, 102 and 104 are intended to form fluid embedding material blocking walls or dams to prevent the fluid embedding material from flowing out of the lower tissue receiving receptacle past the walls 98, 100, 102 and 104 so that the fluid embedding material does not extend beyond the walls and contact an undersurface 94 of the flange 82.

In accordance with the embodiment of the present invention shown in FIGS. 7-10, it has been found that, in practice, when using the embedding ring 17 on commercially available base molds, sometimes the fluid embedding material, particularly paraffin wax, causes the embedding ring 17 to float upwardly thereby forming an embedding material penetrable space between one or more lower planar surfaces 114, 116, 118 or 120 of the downwardly extending walls 98, 100, 102 or 104, causing some of the embedding material to flow outwardly of the downwardly extending walls 98, 100, 102 or 104 causing excess wax to adhere to an undersurface 94 of the flange 82 of the embedding ring 17. This embedding ring floatation sometimes causes the embedding ring 17 to be cocked out of perpendicular alignment with respect to the base mold causing the tissue sample to be out of alignment with respect to the embedding ring. Misalignment of the embedding ring with respect to the base mold is a serious problem since much time and many specimen slides will be lost during microtome use before a complete specimen cross sectional slide can be obtained.

The base mold 80 shown in FIGS. 7-10, in accordance with an important feature of the present invention, includes a continuous trough generally designated 122 completely surrounding a tissue specimen receiving lower mold receptacle, generally designated 14A. Except for this trough 122, the base mold 80 can be manufactured exactly as base mold 10, described with reference to FIGS. 1-6. The trough 122 is adapted to receive the downwardly extending walls 98, 100, 102 and 104 of the embedding ring 17, as shown in FIGS. 9 and 10. The trough 122 is formed in the embedding ring support panels 16A for example by molding the trough 122 to a depth sufficient to receive the walls 98, 100, 102 and 104 downwardly extending from the flange 82 of the embedding ring 17. The panel 16A further is formed, as by molding, to include a pair of spaced circular depressions 126 and 128 having a diameter sufficient to receive the downwardly extending round protuberances 106 and 108 extending downwardly from the flange 82 of the embedding ring 17 so that the undersurface 94 of the flange 82 will contact the upper surface of the panel 16A, as shown in FIGS. 9 and 10.

The trough 122 is formed to completely surround the lower mold receptacle 14A at a location spaced from the lower mold receptacle 14A to form four continuous outer lower mold receptacle wall portions 130, 132, 134 and 136 spaced from inner lower mold receptacle wall portions 18A, 20A, 22A and 24A as best shown in FIGS. 9 and 10. The base mold 80 shown in FIGS. 7-10 includes a pair of extension flanges 138 and 140 extending upwardly and continuously from side walls 137 and 139 and includes a pair of alignment notches 142 and 144 in end wall 52A and a pair of differently spaced alignment notches 146 and 148 in end wall 36A for aligned stacking of one base mold 80 upon another base mold 80. The general shape and configuration of the outer walls of base mold 80 may be the same as that described with reference to FIGS. 1-6 and, likewise, the outer shape and configuration of the base mold shown in FIGS. 1-6 may be the same as that shown in FIGS. 7-10.

The base molds 10 and 80 can be manufactured to accommodate most presently available conventional tissue processing cassettes 12 and embedding rings 17 and can be modified to accommodate any sizes.

Accordingly, the free standing base molds 10 and 80 of the present invention have a number of advantages, some of which have been described above and others of which are inherent in the invention. Also, modifications can be made to the base molds 10 and 80 without departing from the teachings of the present invention.

I claim:

1. A free standing, disposable, unitary base mold formed entirely of press molded, thin, plastic sheet material and having a generally rectangular shaped outer peripheral support wall structure formed with a continuous, supporting lower edge adapted to rest upon a planar surface for supporting said base mold thereon during use:

said base mold including first means forming a lower mold receptacle having a generally rectangular peripheral outline for containing a tissue specimen to be embedded in a tissue embedding material flowed into said lower mold receptacle from above while in a fluid condition and solidifying around said specimen to secure said specimen in a fixed position within said lower mold receptacle, said lower mold receptacle including a planar bottom wall having an underside in coplanar relation with said lower edge of said support wall structure to also rest on said planar surface, said bottom wall having a continuous, outer peripheral edge spaced apart inwardly of said lower edge of said support wall structure and integrally joining an upstanding peripheral side wall;

said base mold further including second means forming an upper mold receptacle for receiving a tissue cassette placed therein after placement of said tissue specimen in said lower mold receptable, said tissue cassette being of a type having a wall adapted to overlie said lower mold receptacle while said cassette is placed in said upper mold receptacle and said cassette wall having at least one aperture therein for communication between said upper and lower mold receptacles for permitting at least some of said fluid embedding material poured into said upper mold receptacle to flow through said aperture into said lower mold receptacle to embed said tissue specimen in said material, said upper mold receptacle including a lower panel for supporting said cassette around edge portions thereof, said panel spaced parallel and above said bottom wall for integrally joining an upper peripheral edge of said upstanding peripheral side wall of said lower mold receptacle and extending outwardly thereof toward said support wall structure, said lower panel of said upper mold receptacle integrally joining an upstanding peripheral side wall of said upper mold receptacle, said peripheral side wall of said upper mold receptacle integrally joining a peripheral rim;

said rim integrally joining said support wall structure, said support wall structure being downwardly and outwardly sloping.

2. A free standing, disposable base mold as set forth in claim 1 wherein said peripheral rim includes a flat surface parallel and spaced above said lower panel of said upper mold receptacle.

3. A free standing, disposable base mold as set forth in claim 2 wherein said rim includes an inner edge portion curved downwardly to integrally join an upper edge of said upstanding peripheral side wall of said upper mold receptacle.

4. A free standing, disposable base mold as set forth in claim 2 wherein said rim includes an outer edge portion curved downwardly to integrally join an upper edge of said peripheral skirt wall.

5. A free standing, disposable base mold as set forth in claim 1 wherein said lower panel of said upper mold receptacle includes a pair of relatively large planar end portions at opposite ends of said lower mold receptacle adapted to underlie and support opposite end portions of said tissue cassette when placed in said upper mold receptacle.

6. A free standing, disposable base mold as set forth in claim 5 wherein said lower panel of said upper mold receptacle includes a pair of selectively small, narrow, planar edge portions extending along opposite sides of said upper mold receptacle adapted to underlie and support opposite side edge portions of said tissue cassette when placed in said upper mold receptacle.

7. The free standing base mold of claim 1 including a continuous depression formed in the lower panel of the upper mold receptacle completely surrounding and spaced from the lower mold receptacle adapted to receive wall members extending downwardly from an embedding ring.

8. The free standing base mold of claim 7 further including a pair of spaced depressions in the lower panel of the upper mold receptacle spaced from said continuous depression for receiving rounded protuberances downwardly extending from an embedding ring so that a planar lower surface of an embedding ring flange can contact said lower panel with the downwardly extending embedding ring walls extending into the continuous depression surrounding the lower mold receptacle and with the rounded protuberances extending into the spaced depressions in said lower panel.

9. A free standing, disposable, unitary base mold formed entirely of press molded transparent plastic sheet material and having a generally rectangular shaped outer peripheral support wall structure formed with a continuous, supporting lower edge adapted to rest upon a planar surface for supporting said base mold thereon during use:

said base mold including first means forming a lower mold receptacle having a generally rectangular peripheral outline for containing a tissue specimen to be embedded in a tissue embedding material flowed into said lower mold receptacle from above while in a fluid condition and solidifying around said specimen to secure said specimen in a fixed position within said lower mold receptacle, said lower mold receptacle including a planar bottom wall having an underside in coplanar relation with said lower edge of said support wall structure to also rest on said planar surface, said bottom wall having a continuous, outer peripheral edge spaced apart inwardly of said lower edge of said support wall structure and integrally joining an upstanding peripheral side-wall;

said base mold further including second means forming an upper mold receptacle for receiving an embedding ring or a tissue, cassette placed therein after placement of said tissue specimen in said lower mold receptacle, said embedding ring or cassette being of a type adapted to overlie said lower mold receptacle while said embedding ring or cassette is placed in said upper mold receptacle for fluid communication between said upper and lower mold receptacles for permitting at least some of said fluid embedding material poured into upper mold receptacle to flow from said lower mold receptacle into said embedding ring or cassette to embed said tissue specimen in said material and to fix the material to the embedding ring or cassette, said upper mold receptacle including a lower panel for supporting said embedding ring or cassette, said panel spaced parallel and above said bottom wall for integrally joining an upper peripheral edge of said upstanding peripheral side wall of said lower mold receptacle and extending outwardly thereof toward said support wall structure, said lower panel of said upper mold receptacle integrally joining an upstanding peripheral side wall of said upper mold receptacle, said peripheral side wall of said upper mold receptacle integrally joining a peripheral rim;

said rim integrally joining said support wall structure, said support structure being downwardly and outwardly sloping.

10. The base mold of claim 9 wherein said lower panel of said upper mold receptacle includes a continuous depression completely surrounding and spaced from the lower mold receptacle.

11. The free standing, disposable base mold as set forth in claim 9 wherein said peripheral rim includes a flat surface parallel and spaced above said lower panel of said upper mold receptacle.

12. A free standing, disposable base mold as set forth in claim 9 wherein said rim includes an inner edge portion curved downwardly to integrally join an upper edge of said upstanding peripheral side wall of said upper mold receptacle.

13. A free standing, disposable base mold as set forth in claim 9 wherein said rim includes an outer edge portion curved downwarly to integrally join an upper edge of said peripheral skirt wall.

14. A free standing, disposable base mold as set forth in claim 9 wherein said lower panel of said upper mold receptacle includes a pair of relatively large planar end portions at opposite ends of said lower mold receptacle adapted to underlie and support opposite end portions of said tissue cassette when placed in said upper mold receptacle.

15. A free standing, disposable base mold as set forth in claim 14 wherein said lower panel of said upper mold receptacle includes a pair of selectively small, narrow planar edge portions extending along opposite sides of said upper mold receptacle adapted to underlie and support opposite side edge portions of said tissue cassette when placed in said upper mold receptacle.

16. The base mold of claim 9 further including a pair of spaced depressions in the lower panel spaced from said continuous depression for receiving rounded protuberances downwardly extending from a flange on an embedding ring so that a planar lower surface of the embedding ring flange can contact the lower panel with the embedding ring walls extending into the continuous depression surrounding the lower mold receptacle and with the rounded protuberances extending into the spaced depressions in the lower panel.

* * * * *